(12) United States Patent
Green et al.

(10) Patent No.: US 6,420,299 B1
(45) Date of Patent: Jul. 16, 2002

(54) BORON-SUBSTITUTED CYCLOPENTADIENES AND METAL COMPLEXES THEREOF

(75) Inventors: D. Patrick Green; Francis J. Timmers, both of Midland; William J. Kruper, Jr., Sanford, all of MI (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 09/568,428

(22) Filed: May 10, 2000

Related U.S. Application Data

(60) Provisional application No. 60/137,766, filed on Jun. 4, 1999.

(51) Int. Cl.$^7$ .............................. B01J 31/38; C08F 4/16; C08F 17/00
(52) U.S. Cl. .................... 502/152; 502/155; 526/127; 526/131; 526/135; 526/160; 526/943; 526/161; 526/348.6; 556/7; 556/11; 556/51; 556/53
(58) Field of Search ..................... 556/7, 11, 51, 556/53; 526/131, 133, 348.6, 943, 160, 161; 502/152, 155

(56) References Cited

U.S. PATENT DOCUMENTS

| | | |
|---|---|---|
| 5,055,438 A | 10/1991 | Canich |
| 5,057,475 A | 10/1991 | Canich et al. |
| 5,064,802 A | 11/1991 | Stevens et al. |
| 5,096,867 A | 3/1992 | Canich |
| 5,132,380 A | 7/1992 | Stevens et al. |
| 5,621,126 A | 4/1997 | Canich et al. |
| 5,703,187 A | 12/1997 | Timmers |
| 5,962,718 A * | 10/1999 | Reetz et al. .................... 556/51 |

FOREIGN PATENT DOCUMENTS

| | | |
|---|---|---|
| EP | 577581 | 1/1994 |
| EP | 416518 | 12/1995 |
| EP | 514828 | 11/1997 |
| GB | 2 303 367 A * | 2/1997 |
| WO | 95/07942 | 3/1995 |
| WO | 96/13529 | 5/1996 |
| WO | WO 97/15581 | 5/1997 |
| WO | WO 98/01485 | 1/1998 |
| WO | WO 98/06727 | 2/1998 |
| WO | WO 98/06728 | 2/1998 |

OTHER PUBLICATIONS

Bochmann et al., Organometallics 1997, 16, 4995–5005.*
"Fe–B bonding in (Dibromoboryl)ferrocene: A Structural and Theoretical Investigation", Andrea Appel et al, Organometallics, 1996, vol. 15, pp. 1188–1194.
"Synthesis, properties, structure and dynamic behavior of pentamethylcyclopentadienyl–substituted boron compounds", Peter Jutzi et al, Chem. Ber., 1987, vol. 120, pp. 565–574 (German language article attached).
Organometallic Chem., E. Barsties et al, vol. 520, pp. 63–68, 1996.
J. Organometallic Chem., H. Plenio et al, vol. 519, pp. 269–272, 1996.
Organometallics, vol. 15, pp. 58–67, 1996.
J. Organomet. Chem., vol. 567 pp. 127–131, 1998.
Organometallics, vol. 16, pp. 4995–5005, 1997.
Organometallics, vol. 15., pp. 2393–2398, 1996.
Organometallics, vol. 15, pp. 5524–5535, 1996.
J.C.S. Chem. Commun., pp. 2081–2082, 1995.
Chimia, vol. 49, p. 501, 1995.

* cited by examiner

*Primary Examiner*—David W. Wu
*Assistant Examiner*—R. Harlan

(57) ABSTRACT

Novel boron-substituted derivatives of cyclopentadiene and metal complexes thereof which are useful in the formulation of catalyst for the polymerization of olefins.

5 Claims, No Drawings

BORON-SUBSTITUTED CYCLOPENTADIENES AND METAL COMPLEXES THEREOF

CROSS REFERENCE STATEMENT

This application claims the benefit of U.S. Provisional Application No. 60/137,766, filed Jun. 4, 1999.

FIELD OF THE INVENTION

This invention relates to boron-substituted derivatives of cyclopentadienes (Cp) and metal complexes thereof which find utility as olefin polymerization catalyst components.

BACKGROUND

Constrained geometry complexes (CGC) and methods for their preparation are disclosed in U.S. Pat. No. 5,703,187, U.S. Pat. No. 5,064,802, U.S. Pat. No. 5,055,438, U.S. Pat. No. 5,057,475, U.S. Pat. No. 5,096,867, U.S. Pat. No. 5,064,802, U.S. Pat. No. 5,132,380, as well as EP-A-514,828, WO 95/00526, and elsewhere. EP-A-577,581 discloses unsymmetrical bis-Cp metallocenes containing a fluorenyl ligand with heteroatom substituents.

E. Barsties; S. Schaible; M.-H. Prosenc; U. Rief; W. Roll; O. Weyland; B. Dorerer; H.-H. Brintzinger *J. Organometallic Chem.* 1996, 520, 63–68, and H. Plenio; D. Birth *J. Organometaic Chem.* 1996, 519, 269–272 disclose non-bridged and Si-bridged ansa bis-indenyl complexes in which the 5 membered ring of the indenyl group is substituted with a dimethylamino substituent. The complexes were disclosed as useful components of catalysts for use in the formation of polyethylene and isotactic polypropylene.

Disclosure of random heteroatom substitution in mono-Cp metallocenes is found in EP-A-416,815, WO 95/07942, WO 96/13529, and U.S. Pat. No. 5,096,867 and U.S. Pat. No. 5,621,126. Specific heteroatom substitution of the 3- and 2-position of indenyl complexes of group 4 metals was disclosed in WO98/06727 and WO/98/06728 respectively. Additional pertinent disclosure may be found in *Organometallics*, 1966, 15, pp 58–67, *J. Organomet. Chem.*, 1998, 567, pp 127–131; *Organometallics*, 1997, 16, pp 4995–5005; *Organometallics*, 1996, 15, pp 2393–2398; *Organometallics*, 1996, 15, pp 5524–5535; *J. C. S. Chem. Commun.*, 1995, pp 2081–2082; WO 97/15581, and *Chimia*, 1995, 49, pg 501.

The foregoing specifically substituted metal complexes have produced improved catalyst results, however, problems still remain with catalyst efficiency and deactivation of the catalyst under high temperature polymerization conditions. It would be advantageous to be able to produce polyolefins with higher molecular weights. It would also be advantageous to be able to improve other physical characteristics of the polymers produced by altering the substitution around the cyclopentadienyl group of the metallocene complexes used in olefin polymerization catalyst systems.

SUMMARY OF THE INVENTION

The present invention provides novel boron-substituted derivatives of cyclopentadienes corresponding to the formula:

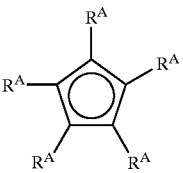

I where, $R^A$ independently each occurrence is hydrogen or $R^B$;

$R^B$ is $BR^C{}_2$, or a hydrocarbyl, hydrocarbylsilyl, halo-substituted hydrocarbyl, hydrocarbyloxy-substituted hydrocarbyl, di(hydrocarbyl)amino-substituted hydrocarbyl, $BR^C{}_2$-substituted hydrocarbyl, hydrocarbylsilylhydrocarbyl, di(hydrocarbyl)amino, hydrocarbadiylamino, or hydrocarbyloxy group, each $R^B$ having from 1 to 80 atoms not counting hydrogen, and optionally two $R^B$ groups may be covalently linked to form one or more fused rings; and $R^C$ independently each occurrence is hydrocarbyl, halo-substituted hydrocarbyl, hydrocarbyloxy-substituted hydrocarbyl, dihydrocarbylamino-substituted hydrocarbyl, hydrocarbadiylamino-substituted hydrocarbyl, hydrocarbylsilyl, hydrocarbylsilylhydrocarbyl, or $R^D$;

$R^D$ independently each occurrence is a dihydrocarbylamino or a hydrocarbyloxy group having from 1 to 20 nonhydrogen atoms, and optionally two $R^D$ groups on a single boron together form a hydrocarbadiylamino-, hydrocarbadiyloxy, hydrocarbadiyldiamino-, or hydrocarbadiyldioxy-group having both valences bound to boron; with the proviso that in at least one occurrence $R^A$ is selected from $BR^C{}_2$, a $BR^C{}_2$-substituted hydrocarbyl group, and joined derivatives thereof, wherein at least one $R^C$ is $R^D$.

This invention also provides derivatives of the aforementioned complexes in the form of:

(A) a Group 1 metal salt derivative;

(B) a Grignard derivative: or (C) a monosilylated anion or disilylated dianion derivative.

Within the scope of this aspect of the invention is the use of one of the foregoing derivatives for synthesis to produce a metal complex of this invention, or, more specifically, the use of one of these derivatives for synthesis to produce a metal complex comprising a metal from one of Groups 3 to 13 of the Periodic Table of the Elements, the lanthanides or actinides, and from 1 to 4 ligands derived from one or more of the foregoing derivatives.

The present invention further provides metal complexes corresponding to the formula:

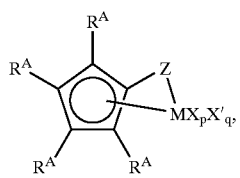

II

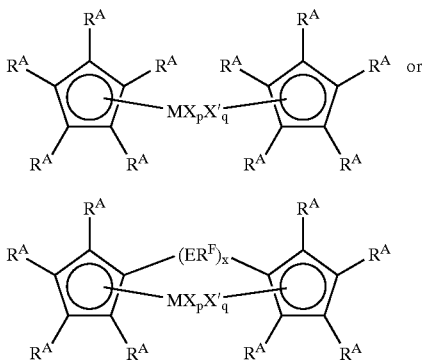

III

IV wherein M is a metal from one of Groups 3 to 13 of the Periodic Table of the Elements, the lanthanides or actinides, Z is a divalent moiety comprising boron, or a member of Group 14 of the Periodic Table of the Elements, and also comprising nitrogen, phosphorus, sulfur or oxygen;

X is an anionic ligand group having up to 60 atoms not counting hydrogen, and optionally 2 X groups together form a divalent anionic ligand group;

X' independently each occurrence is a neutral Lewis base ligand having up to 20 atoms;

p is a number from 0 to 5, and is two less than the formal oxidation state of M;

q is zero, 1 or 2;

E is silicon or carbon, $R^F$ independently each occurrence is hydrogen or a group selected from silyl, hydrocarbyl, hydrocarbyloxy and combinations thereof, said $R^F$ having up to 30 carbon or silicon atoms, and x is 1 to 8, or optionally $(R^F{}_2E)_x$ is —T'Z'— or —(T'Z')$_2$—, wherein, T' independently each occurrence is boron or aluminum, and Z' independently each occurrence is:

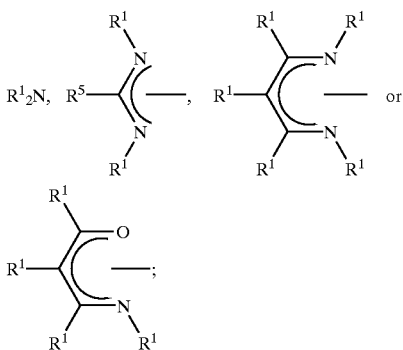

$R^1$ is independently each occurrence hydrogen, a hydrocarbyl group, a trihydrocarbylsilyl group, or a trihydrocarbylsilylhydrocarbyl group, said $R^1$ groups containing up to 20 atoms not counting hydrogen, and two such $R^1$ groups may optionally be joined together to form a ring structure; and $R^5$ is $R^1$ or $N(R^1)_2$.

The above metal complexes may exist as isolated crystals optionally in pure form or as a mixture (including as a mixture with other complexes), in the form of a solvated adduct, optionally in a solvent, especially an organic liquid, as well as in the form of a dimer or chelated derivative thereof.

Also, according to the present invention, there is provided a catalyst composition for olefin polymerization prepared from catalyst system components comprising:

(A) a metal complex of one or more of the aforementioned Formulae II, III, or IV; and (B) an activating cocatalyst wherein the molar ratio of (A) to (B) is from 1:10,000 to 100:1.

Another embodiment of this invention is a catalyst composition for olefin polymerization prepared from catalyst system components comprising:

(A) a metal complex of one or more of the aforementioned metal complexes of Formulae II, III, or IV; and (B) a an activating cocatalyst wherein the molar ratio of (A) to (B) is from 1:10,000 to 100:1, wherein the metal complex is in the form of a radical cation.

Further according to the present invention there is provided a process for the polymerization of olefins comprising contacting one or more $C_{2-20}$ α-olefins under polymerization conditions with one of the aforementioned catalyst compositions.

A preferred process of this invention is a high temperature solution polymerization process for the polymerization of olefins comprising contacting one or more $C_{2-20}$ α-olefins under polymerization conditions with one of the aforementioned catalyst compositions at a temperature from 100° C. to 250° C.

Within the scope of this invention are the polyolefin products produced by the aforementioned processes. Preferred products have long chain branching and reverse moleculararchitecture.

The present catalysts and processes result in the highly efficient production of high molecular weight olefin polymers over a wide range of polymerization conditions, and especially at elevated temperatures. They are especially useful for the solution or bulk polymerization of ethylene/propylene (EP polymers), ethylene/octene (EO polymers), ethylene/styrene (ES polymers), propylene and ethylene/propylene/diene (EPDM polymers) wherein the diene is ethylidenenorbornene, 1,4-hexadiene or similar nonconjugated diene. The use of elevated temperatures dramatically increases the productivity of such processes due to the fact that increased polymer solubility at elevated temperatures allows the use of increased conversions (higher concentration of polymer product) without exceeding solution viscosity limitations of the polymerization equipment as well as reduced energy costs needed to devolatilize the reaction product.

The catalyst compositions of this invention may also include a support material and may be used in olefin polymerization processes in a slurry or in the gas phase. The catalyst may be prepolymerized with one or more olefin monomers in situ in a polymerization reactor or in a separate process with intermediate recovery of the prepolymerized catalyst prior to the primary polymerization process.

DETAILED DESCRIPTION

All reference to the Periodic Table of the Elements herein shall refer to the Periodic Table of the Elements, published and copyrighted by CRC Press, Inc., 1997. Also, any reference to a Group or Groups shall be to the Group or Groups as reflected in this Periodic Table of the Elements using the IUPAC system for numbering groups. The full teachings of any patent, patent application, provisional application, or publication referred to herein are hereby incorporated by reference. The term "reverse molecular architecture" as used herein refers to a copolymer of two or more olefins wherein higher molecular weight fractions of the polymer contain increased content of the higher molecular weight comonomer.

The novel boron-substituted derivatives of cyclopentadienes of the invention are prepared from starting materials known in the literature.

Preferred boron-substituted derivatives of cyclopentadienes of the present invention and metal complexes thereof, correspond to the formulas I, II and III, wherein $R^A$ in at least one occurrence in the compound and at most in one occurrence per each cyclopentadienyl ring system in the compound is $B(NR^E{}_2)_2$, $BR^E(NR^E{}_2)$, $B(OR^E)_2$, $BR^E(OR^E)$, or $B(OR^E)(NR^E{}_2)$, wherein $R^E$ is a hydrocarbyl group containing from 1–20 carbon atoms or two $R^E$ groups in the same boron ligand together form a hydrocarbylene group.

Most preferred boron-substituted derivatives of cyclopentadienes of the present invention correspond to the formula:

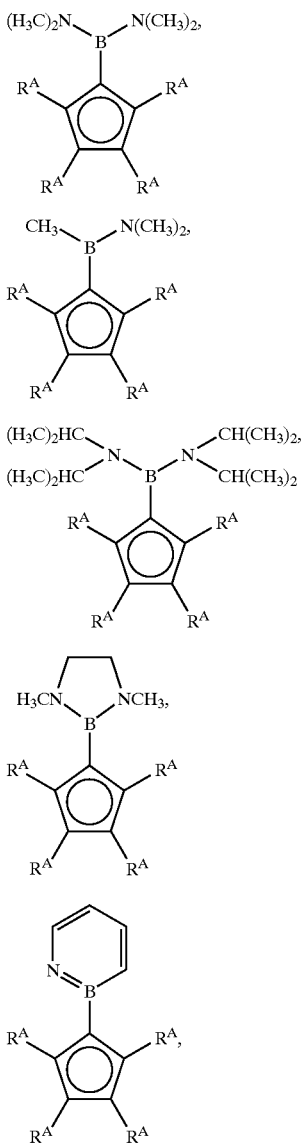

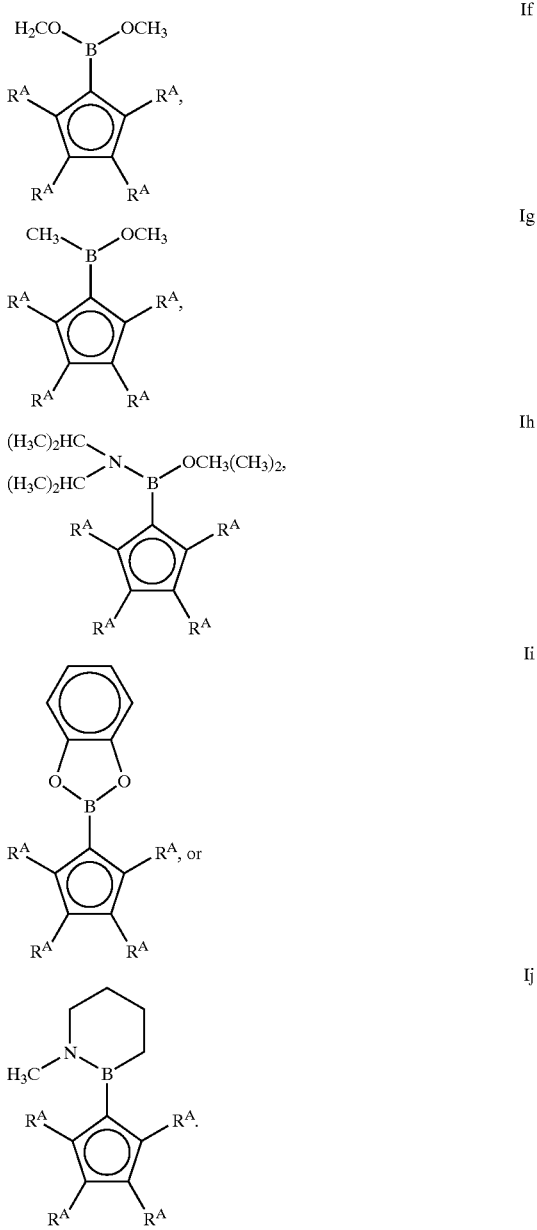

A variety of metals can be used in the preparation of the metal complexes of this invention, desirably a metal from one of Groups 3 to 13 of the Periodic Table of the Elements, the lanthanides or abinides, which is in the +2, +3 or +4 formal oxidation state, more desirably a metal from one of Groups 3 to 5. Preferred are those metal complexes where M is a metal from Group 4, (Ti, Zr or Hf), with Ti and Zr being most highly preferred.

Preferred X' groups are carbon monoxide; phosphines, especially trimethylphosphine, triethylphosphine, triphenylphosphine and bis (1,2-dimethylphosphino)ethane; $P(OR^i)_3$, wherein $R^i$ is hydrocarbyl, silyl or a combination thereof; ethers, especially tetrahydrofuran; amines, especially pyridine, bipynidine, tetramethylethylenediamine (TMEDA), and triethylamine; olefins; and conjugated dienes having from 4 to 40 carbon atoms. Complexes including conjugated diene X' groups include those wherein the metal is in the +2 formal oxidation state.

Preferred X groups include hydride, halide and alkyl, alkenyl, aryl, or cycloalkyl groups of from 1 to 10 carbons, or two X groups together are an alkenediyl group. Preferred —Z— groups are —(Z*—Y)—, with Z* bonded to the boron-substituted cyclopentadienyl group and Y* bonded to M, and Y* is —O—, —S—, —NR*—, —NR*$_2$—, —PR*—;

Z* is SiR*$_2$, CR*$_2$, SiR*$_2$SiR*$_2$, CR*$_2$CR*$_2$, CR*=CR*, CR*$_2$SiR*$_2$, CR*$_2$SiR*$_2$CR*$_2$, SiR*$_2$CR*$_2$SiR*$_2$, CR*$_2$CR*$_2$SiR*$_2$, CR*$_2$CR*$_2$CR*$_2$, B—NR*$_2$ or GeR*$_2$; and R* independently each occurrence is hydrogen, or a member selected from hydrocarbyl, hydrocarbyloxy, silyl, halogenated alkyl, halogenated aryl, and combinations thereof, said R* having up to 20 atoms not counting hydrogen, and optionally, two R* groups from Z (when R* is not hydrogen), or an R* group from Z and an R* group from Y form a ring system.

Preferred coordination complexes according to the present invention are complexes corresponding to formulas II, III and IV, wherein M is titanium or zirconium, the non-boron containing R$^A$ groups are hydrogen, dimethylamino, pyrrolidino, or hydrocarbyl, or two such adjacent R$^A$ groups are joined together, thereby forming an indenyl, fluorenyl, s-indacenyl, or tetrahydrofluorenyl ligand;

when p is 2, X is chloride, methyl, benzyl, or cyclopentadienyl, or two X groups together are a 2-butene-1,4-diyl, or 2,3-dimethyl-2-butene-1,4-diyl group;

when p is 1, X is 2-(N,N-dimethylamino)phenyl or allyl, and when p is 0, q is 1, and X' is 1,4-diphenyl-1,3-butadiene or 1,3-pentadiene.

In another aspect of this invention it is preferred that Y is —NR*, with the more preferred —NR* being those where R* is a group having a primary or secondary carbon atom bonded to N. Highly preferred are compounds where R* is cyclohexyl or isopropyl.

The metal complexes of the present invention that result in highly active polymerization catalysts when combined with an activating cocatalyst preferably correspond to the formula:

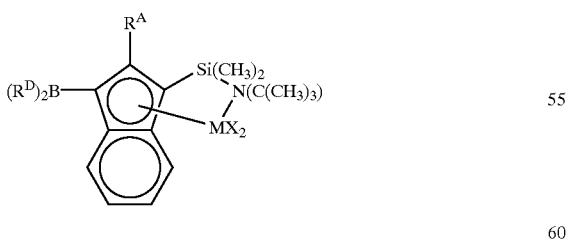

wherein R$^D$ is N,N-dimethylamino or N,N-diisopropylamino, R$^A$ is methyl or hydrogen, M is titanium, and X is chloride or methyl.

Illustrative metal complexes of the present invention include:

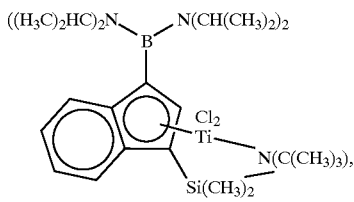

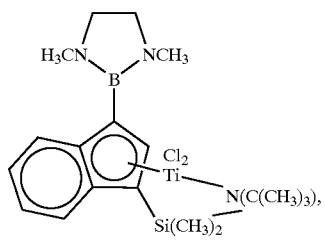

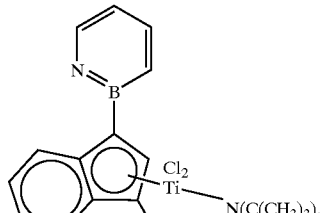

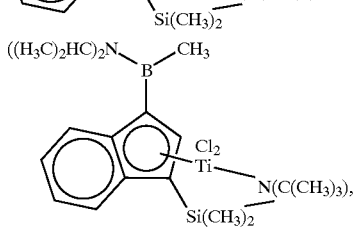

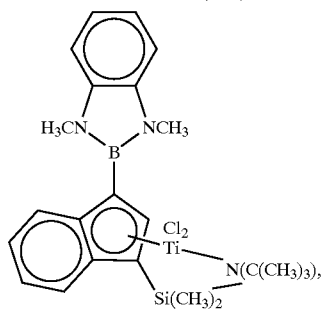

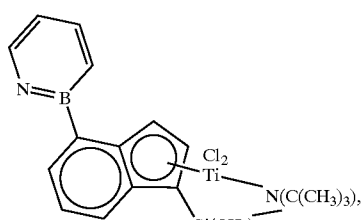

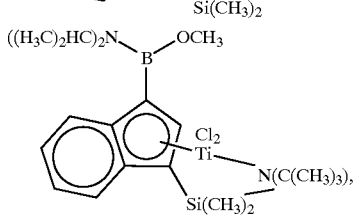

-continued

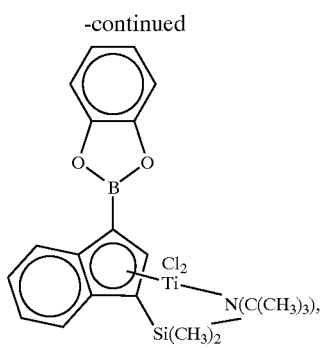

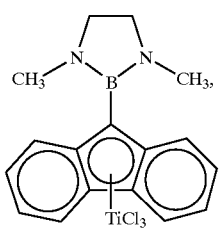

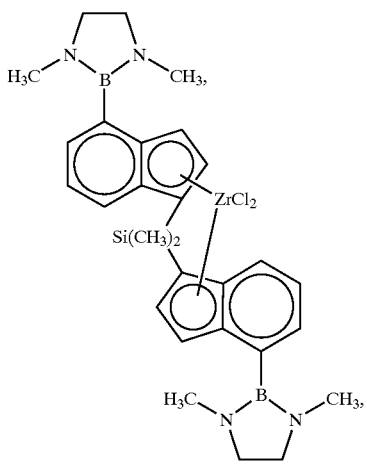

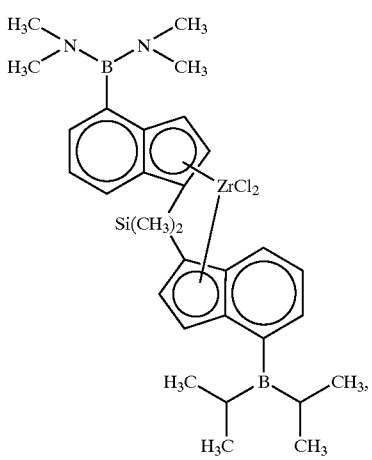

-continued

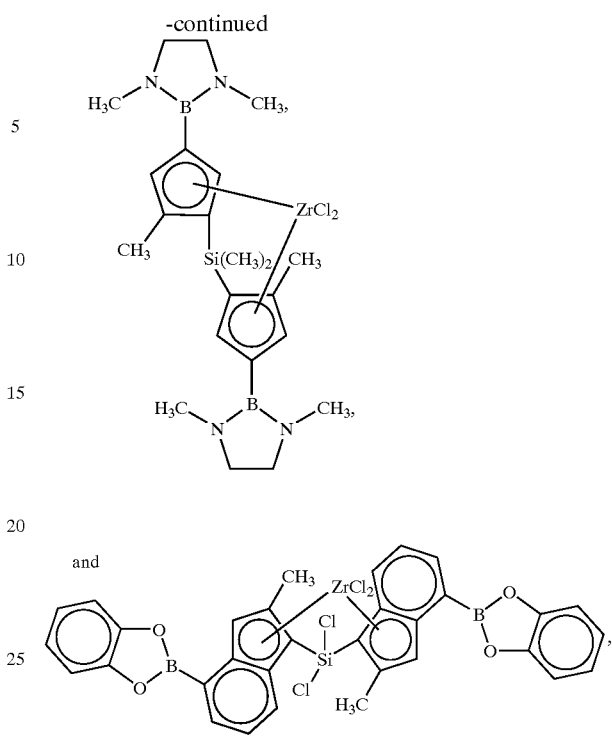

or the foregoing complexes wherein one or more chlorides are replaced by methyl or benzyl groups, or two chlorides are replaced by a neutral 1,4-diphenyl-1,3-butadiene or a 1,3-pentadiene ligand.

The metal complexes can be prepared by use of well known synthetic techniques. Optionally a reducing agent can be employed to produce the lower oxidation state complexes. Such a process is disclosed in U.S. Pat. No. 5,470,993. The reactions are conducted in a suitable noninterfering solvent at a temperature from −100 to 300° C., preferably from −78 to 150° C., most preferably from 0 to 50° C. By the term "reducing agent" herein is meant metal or compound which, under reducing conditions causes the metal M, to be reduced from a higher to a lower oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, lithium or potassium alkadienyls; and Grignard reagents. Most preferred reducing agents are the alkali metals or alkaline earth metals, especially lithium and magnesium metal.

Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable.

A general method for producing the titanium(II)diene complex from the corresponding titanium(IV)dichloride preferably involves the treatment of the dichloride with n-butyl lithium in the presence of an appropriate diene. A similar technique has been described in *Organometallics*, 1995, 14, 3132–3134 as well as in U.S. Pat. No. 5,556,928.

The formation of the metal complexes wherein the metal is in the +3 formal oxidation state according to the invention can be accomplished by any of several synthesis methods. One technique involves the reaction under anaerobic and anhydrous conditions of metallated derivatives of the complexes or bridged derivatives thereof with trivalent metal salts, such as Group 4 metal (III) halide or alkoxide complexes, optionally followed by silylation or hydrocarbylation with suitable silylating or hydrocarbylating agents, to form the corresponding halide, alkoxide, silyl or hydrocarbyl complexes of the invention. A further synthesis method involves reducing an appropriate metal (IV) complex with a suitable reducing agent to the corresponding metal (III) complex. Suitable reducing agents especially include zinc, aluminum and magnesium.

Suitable silylating and hydrocarbylating agents for the metal complexes of the invention include the corresponding silyl or hydrocarbyl derivatives of Group 1, 2 or 13 metals or Group 2 metal halides, preferably lithium sodium, potassium, magnesium and aluminum, or Group 2 metal Grignards. Examples of suitable hydrocarbyl an silyl groups include alkyl, such as methyl, ethyl, propyl, butyl, neopentyl and hexyl; aryl, such as phenyl, naphthyl and biphenyl; aralkyl, such as benzyl, tolylmethyl, diphenylmethyl; alkaryl, such as tolyl and xylyl; allyl; silyl- or alkyl-substituted allyl, such as methylallyl, trimethylsilylallyl, dimethylallyl and trimethylallyl; trialkylsilyl, such as trimethylsilyl and triethylsilyl; trialkylsilylalkyl, such as trimethylsiiylmethyl; pentadienyl; alkyl- or silyl-substituted pentadienyl, such as methylpentadienyl, dimethylpentadienyl, trimethylsilylpentadienyl, bis(trimethylsilyl)pentadienyl, cyclohexadienyl and dimethylcyclohexadienyl; dialkylaminoalkaryl, such as o-(N,N-dimethylaminomethyl)phenyl; and dialkylaminoaralkyl, such as o-(N,N-dimethylamino)benzyl. Preferred silylating and hydrocarbylating agents include trimethylaluminum, methyllithium, methyl magnesium chloride, neopentyllithium, trimethylsilylmethyl magnesium chloride and phenyllithium. Stabilizing group-containing hydrocarbylating agents are also included, especially the stabilizing group-containing hydrocarbylating agents and salts of the stabilizing group-containing hydrocarbyl groups described in U.S. Pat. No. 5,504,224, whose salts include, for example, benzyl potassium, 2-(N,N-dimethylamino)benzyllithium, aliyllithium and dimethylpentadienyl potassium. Such stabilizing groups are further described in U.S. Pat. No. 5,374,696, and elsewhere.

The complexes are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-45}$ hydrocarbyl substituted Group 13 compounds, especially tri(hydrocarbyl)aluminum- or tri(hydrocarbyl)boron compounds and halogenated (including perhalogenated) derivatives thereof, having from 1 to 15 carbons in each hydrocarbyl or halogenated hydrocarbyl group, more especially perfluorinated tri(aryl)boron compounds, and most especially tris(o-nonafluorobiphenyl)borane, tris(pentafluorophenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalsts and activating techniques have been previously taught with respect to different metal complexes in EP-A-277,003 and U.S. Pat. No. 5,153,157, U.S. Pat. No. 5,064,802, U.S. Pat. No. 5,321,106, and U.S. Pat. No. 5,721,185.

Combinations of neutral Lewis acids, especially the combination of a trialkyl aluminum compound having from 1 to 4 carbons in each alkyl group and a halogenated tri (hydrocarbyl)boron compound having from 1 to 20 carbons in each hydrocarbyl group, especially tris(pentafluorophenyl)borane, tris(o-nonafluorobiphenyl) borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. A benefit according to the present invention is the discovery that the most efficient catalyst activation using such a combination of tris(pentafluorophenyl)borane/alumoxane mixture occurs at reduced levels of alumoxane. Preferred molar ratios of metal complex: tris(pentafluorophenyl)borane: alumoxane are from 1:1:1 to 1:5:5, more preferably from 1:1:1.5 to 1:5:3. The surprising efficient use of lower levels of alumoxane with the present invention allows for the production of olefin polymers with high catalytic efficiencies using less of the expensive alumoxane cocatalyst. Additionally, polymers with lower levels of aluminum residue, and hence greater clarity, are obtained.

Suitable ion forming compounds useful as cocatalysts in one embodiment of the present invention comprise a cation which is a Bronsted acid capable of donating a proton, and a compatible, noncoordinating anion, $A^-$. As used herein, the term "noncoordinating" means an anion or substance which either does not coordinate to the metal complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

$$(L^*—H)_d^+(A)^{d-}$$

wherein:
L* is a neutral Lewis base;
(L*—H)+ is a Bronsted acid;
$(A)^{d-}$ is a noncoordinating, compatible anion having a charge of d−, and
d is an integer from 1 to 3.

More preferably $(A)^{d-}$ corresponds to the formula: $[M'Q_4]^-$;
wherein:
M' is boron or aluminum in the +3 formal oxidation state; and
Q independently each occurrence is selected from hydride, dialkylamido, halide, hydrocarbyl, hydrocarbyloxide, halosubstituted-hydrocarbyl, halo-substituted hydrocarbyloxy, and halo-substituted silylhydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433.

In a more preferred embodiment, d is one, that is, the counter ion has a single negative charge and is A⁻. Activating cocatalysts comprising boron which are particularly useful in the preparation of catalysts of this invention may be represented by the following general formula:

$$(L^*—H)^+(BQ_4)^-;$$

wherein:
L* is as previously defined;
B is boron in a formal oxidation state of 3; and
Q is a hydrocarbyl-, hydrocarbyloxy-, fluorinated hydrocarbyl-, fluorinated hydrocarbyloxy-, or fluorinated silylhydrocarbyl-group of up to 20 nonhydrogen atoms, with the proviso that in not more than one occasion is Q hydrocarbyl.

Most preferably, Q is each occurrence a fluorinated aryl group, especially, a pentafluorophenyl group.

Illustrative, but not limiting, examples of ion forming compounds comprising proton donatable cations which may be used as activating cocatalysts in the preparation of the catalysts of this invention are tri-substituted ammonium salts such as:
trimethylammonium tetraphenylborate,
methyldioctadecylammonium tetraphenylborate,
triethylammonium tetraphenylborate,
tripropylammonium tetraphenylborate,
tri(n-butyl)ammonium tetraphenylborate,
methyltetradecyloctadecylammonium tetraphenylborate,
N,N-dimethylanilinium tetraphenylborate,
N,N-diethylanilinium tetraphenylborate,
N,N-dimethyl(2,4,6-trimethylanilinium) tetraphenylborate,
trimethylammonium tetrakis(penta-fluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-diethylanilinium tetrakis(pentafluorophenyl)borate,
N,N-dimethyl(2,4,6-tnimethylanilinium)tetrakis(pentafluorophenyl)borate,
trimethylammonium tetrakis(2,3,4,6-tetrafluorophenyl)borate,
triethylammonium tetrakis(2,3,4,6-tetrafluorophenyl)borate,
tripropylammonium tetrakis(2,3,4,6-tetrafluorophenyl)borate,
tri(n-butylammonium tetrakis(2,3,4,6-tetrafluorophenyl)borate,
dimethyl(t-butyl)ammonium tetrakis(2,3,4,6-tetrafluorophenyl)borate,
N,N-dimethylanilinium tetrakis(2,3,4,6-tetrafluorophenyl)borate,
N,N-diethylanilinium tetrakis(2,3,4,6-tetrafluorophenyl)borate, and
N,N-dimethyl-(2,4,6-trimethylanilinium)tetrakis-(2,3,4,6-tetrafluorophenyl)borate.

Dialkyl ammonium salts such as:
di-(i-propyl)ammonium tetrakis(pentafluorophenyl)borate, and
dicyclohexylammonium tetrakis(pentafluorophenyl)borate.

Tri-substituted phosphonium salts such as:
triphenylphosphonium tetrakis(pentafluorophenyl)borate,
tri(o-tolyl)phosphonium tetrakis(pentafluorophenyl)borate, and
tri(2,6-dimethylphenyl)phosphonium tetrakis(pentafluorophenyl)borate.

Preferred are tetrakis(pentafluorophenyl)borate salts of long chain alkyl mono- and disubstituted ammonium complexes, especially $C_{14}$–$C_{20}$ alkyl ammonium complexes, especially methyldi(octadecyl)ammonium tetrakis(pentafluorophenyl)borate and methyldi(tetradecyl)ammonium tetrakis(pentafluorophenyl)borate.

An especially preferred group of activating cocatalysts is trs(pentafluorophenyl)borane, N—$R_3$,N—$R_4$ aniinium tetrakis(pentafluorophenyl)borate where $R_3$ and $R_4$ independently each occurrence are substituted or unsubstituted saturated hydrocarbyl groups having from 1 to 8 carbon atoms, $(R_1R_2NHCH_3)^+(C_6H_4OH)B(C_6F_5)_3^-$, or $(R_1R_2NHCH_3)^+B(C_6F_5)_4^-$, where $R_1$ and $R_2$ independently each occurrence are substituted or unsubstituted saturated hydrocarbyl groups having from 12 to 30 carbon atoms.

Another suitable ion forming, activating cocatalyst comprises a salt of a cationic oxidizing agent and a noncoordinating, compatible anion represented by the formula:

$$(Ox^{e+})_d(A^{d-})_e.$$

wherein:
$Ox^{e+}$ is a cationic oxidizing agent having a charge of e+;
e is an integer from 1 to 3; and
$A^{d-}$ and d are as previously defined.

Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activating cocatalysts, especially tetrakis (pentafluorophenyl)borate.

Another suitable ion forming, activating cocatalyst comprises a compound which is a salt of a carbenium ion and a noncoordinating, compatible anion represented by the formula:

$^+A^-$ wherein:

$^+$ is a $C_{1-20}$ carbenium ion; and $A^-$ is as previously defined. A preferred carbenium ion is the trityl cation, i.e. triphenylmethylium.

A further suitable ion forming, activating cocatalyst comprises a compound which is a salt of a silylium ion and a noncoordinating, compatible anion represented by the formula:

$$R_3Si^+A^-$$

wherein:

R is $C_{1-10}$ hydrocarbyl, and $A^-$ are as previously defined.

Preferred silylium salt activating cocatalysts are trimethylsilylium tetrakispentafluorophenylborate, triethylsilylium tetrakispentafluorophenylborate and ether substituted adducts thereof. Silylium salts have been previously generically disclosed in *J. Chem Soc. Chem. Comm.*, 1993, 383–384, as well as Lambert, J. B., et al., *Organometallics*, 1994, 13, 2430–2443. The use of the above silylium salts as activating cocatalysts for addition polymerization catalysts is disclosed in U.S. Pat. No. 5,625,087.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0 to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), dimethoxyethane (DME), and mixtures thereof.

The electrolysis may be conducted in a standard electrolytic cell containing an anode and cathode (also referred to as the working electrode and counter electrode respectively). Suitable materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and a compatible, noncoordinating anion, A–.

Preferred supporting electrolytes are salts corresponding to the formula $G^+A^-$; wherein:

$G^+$ is a cation which is nonreactive towards the starting and resulting complex, and $A^-$ is as previously defined.

Examples of cations, $G^+$, include tetrahydrocarbyl substituted ammonium or phosphonium cations having up to 40 nonhydrogen atoms. Preferred cations are the tetra(n-butylammonium)- and tetraethylammoniumcations.

During activation of the complexes of the present invention by bulk electrolysis the cation of the supporting electrolyte passes to the counter electrode and $A^-$ migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoroaryl)borates having from 1 to 10 carbons in each hydrocarbyl or perfluoroaryl group, especially tetra(n-butylammonium)tetrakis(pentafluorophenyl)borate.

A further recently discovered electrochemical technique for generation of activating cocatalysts is the electrolysis of a disilane compound in the presence of a source of a noncoordinating compatible anion. This technique is more fully disclosed in U.S. Pat. No. 5,372,682.

The foregoing electrochemical activating technique and activating cocatalysts may also be used in combination. An especially preferred combination is a mixture of a tri (hydrocarbyl)aluminum or tri(hydrocarbyl)borane compound having from 1 to 4 carbons in each hydrocarbyl group with an oligomeric or polymeric alumoxane compound.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris (pentafluorophenyl)borane, where used as an activating cocatalyst, is employed in a molar ratio to the metal complex of form 0.5:1 to 10:1, more preferably from 1:1 to 6:1, most preferably from 1:1 to 5:1. The remaining activating cocatalysts are generally employed in approximately equimolar quantity with the metal complex.

Suitable polymerizable monomers include ethylenically unsaturated monomers, acetylenic compounds, conjugated or non-conjugated dienes, and polyenes. Preferred monomers include olefins, for examples alpha-olefins having from 2 to 20,000, preferably from 2 to 20, more preferably from 2 to 8 carbon atoms and combinations of two or more of such alpha-olefins. Particularly suitable alpha-olefins include, for example, ethylene, propylene, 1-butene, 1-pentene, 4-methylpentene-1,1-hexene, 1-heptene, 1-octene, 1-nonene, 1-decene, 1-undecene, 1-dodecene, 1-tridecene, 1-tetradecene, 1-pentadecene, or combinations thereof, as well as long chain vinyl terminated oligomeric or polymeric reaction products formed during the polymerization, and $C_{10-30}$ α-olefins specifically added to the reaction mixture in order to produce relatively long chain branches in the resulting polymers. Preferably, the alpha-olefins are ethylene, propene, 1-butene, 4-methyl-pentene-1,1-hexene, 1-octene, and combinations of ethylene and/or propene with one or more of such other alpha-olefins. Other preferred monomers include styrene, halo- or alkyl substituted styrenes, tetrafluoroethylene, vinylcyclobutene, 1,4-hexadiene, dicyclopentadiene, ethylidene norbomene, and 1,7-octadiene. Mixtures of the above-mentioned monomers may also be employed.

In general, the polymerization may be accomplished at conditions well known in the prior art for solution phase, slurry, gas phase and high pressure Ziegler-Natta or Kaminsky-Sinn type polymerization reactions. Examples of such well known polymerization processes are depicted in U.S. Pat. No. 5,084,534, U.S. Pat. No. 5,405,922, U.S. Pat. No. 4,588,790, U.S. Pat. No. 5,032,652, U.S. Pat. No. 4,543,399, U.S. Pat. No. 4,564,647, U.S. Pat. No. 4,522,987, and elsewhere. Preferred polymerization temperatures are from 0–250° C. Preferred polymerization pressures are from atmospheric to 3000 atmospheres. Molecular weight control agents can be used in combination with the present cocatalysts. Examples of such molecular weight control agents include hydrogen, silanes or other known chain transfer agents. The catalyst composition may be used by itself (homogeneously) or supported on an inert support such as silica, alumina or a polymer. The skilled artisan will appreciate that the invention disclosed herein may be practiced in the absence of any component which has not been specifically disclosed.

What is claimed is:

1. A metal complex corresponding to the formula:

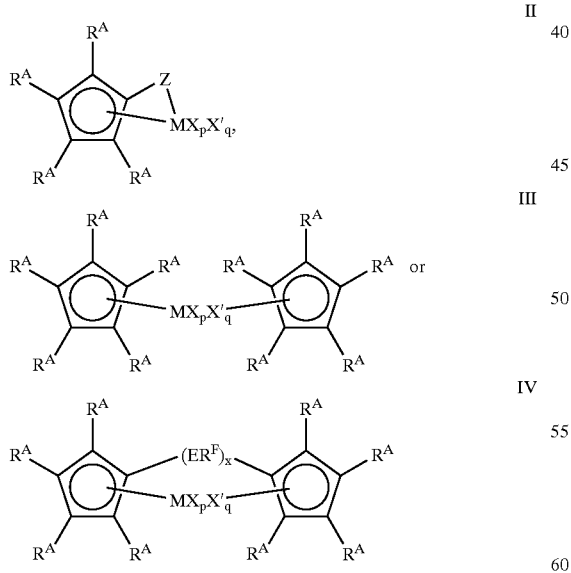

wherein M is a metal from one of Groups 3 to 13 of the Periodic Table of the Elements, the lanthanides or actinides, Z is a divalent moiety comprising boron, or a member of Group 14 of the Periodic Table of the Elements, and also comprising nitrogen, phosphorus, sulfur or oxygen;

X is an anionic ligand group having up to 60 atoms not counting hydrogen, and optionally 2 X groups together form a divalent anionic ligand group;

X' independently each occurrence is a neutral Lewis base ligand having up to 20 atoms;

p is a number from 0 to 5, and is two less than the formal oxidation state of M;

q is zero, 1 or 2;

E is silicon or carbon, $R^A$ independently each occurrence is hydrogen or $R^B$;

$R^B$ is $BR^C{}_2$, or a hydrocarbyl, hydrocarbylsilyl, halo-substituted hydrocarbyl, hydrocarbyloxy-substituted hydrocarbyl, di(hydrocarbyl)amino-substituted hydrocarbyl, $BR^C{}_2$-substituted hydrocarbyl, hydrocarbylsilylhydrocarbyl, di(hydrocarbyl)amino, hydrocarbadiylamino, or hydrocarbyloxy group, each $R^B$ having from 1 to 80 atoms not counting hydrogen, and optionally two $R^B$ groups may be covalently linked to form one or more fused rings; and $R^C$ independently each occurrence is hydrocarbyl, halo-substituted hydrocarbyl, hydrocarbyloxy-substituted hydrocarbyl, dihydrocarbylamino-substituted hydrocarbyl, hydrocarbadiylamino-substituted hydrocarbyl, hydrocarbylsilyl, hydrocarbylsilylhydrocarbyl, or $R^D$;

$R^D$ independently each occurrence is a dihydrocarbylamino group having from 1 to 20 nonhydrogen atoms, and optionally two $R^D$ groups on a single boron together form a hydrocarbadiylamino- or hydrocarbadiyldiamino-group having both valences bound to boron;

with the proviso that in at least one occurrence $R^A$ is selected from $BR^C{}_2$, a $BR^C{}_2$-substituted hydrocarbyl group, or joined derivatives thereof, wherein at least one $R^C$ is $R^D$;

$R^F$ independently each occurrence is hydrogen or a group selected from silyl, hydrocarbyl, hydrocarbyloxy and combinations thereof, said $R^F$ having up to 30 carbon or silicon atoms, and x is 1 to 8, or optionally $(R^F{}_2E)_x$ is —T'Z'— or —(T'Z')$_2$—, wherein, T' independently each occurrence is boron or aluminum, and Z' independently each occurrence is:

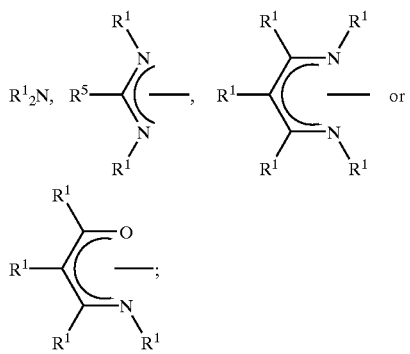

$R^1$ is independently each occurrence hydrogen, a hydrocarbyl group, a trihydrocarbylsilyl group, or a trihydrocarbylsilylhydrocarbyl group, said $R^1$ groups containing up to 20 atoms not counting hydrogen, and two such $R^1$ groups may optionally be joined together to form a ring structure; and $R^5$ is $R^1$ or $N(R^1)_2$.

2. The metal complex of claim 1 wherein $R^A$ in at least one occurrence in the compound and at most in one occurrence per each cyclopentadienyl ring system in the compound is $B(NR^E_2)_2$ or $BR^E(NR^E_2)$ wherein $R^E$ is a hydrocarbyl group containing from 1–20 carbon atoms or two $R^E$ groups in the same boron ligand together form a hydrocarbylene group.

3. The metal complex of claim Z, wherein —Z— is —(Z*—Y)—, with Z* bonded to Cp and Y bonded to M, and Y is —O—, —S—, —NR*—, —NR*$_2$, or —PR*—;

Z* is $SiR^*_2$, $CR^*_2$, $SiR^*_2SiR^*_2$, $CR^*_2CR^*_2$, $CR^*=CR^*$, $CR^*_2SiR^*_2$, $CR^*_2SiR^*_2CR^*_2$, $SiR^*_2CR^*_2SiR^*_2$, $CR^*_2CR^*_2SiR^*_2$, $CR^*_2CR^*_2CR^*_2$, or $GeR^*_2$; and R* independently each occurrence is hydrogen, or a member selected from hydrocarbyl, hydrocarbyloxy, silyl, halogenated alkyl, halogenated aryl, and combinations thereof, said R* having up to 20 atoms not counting hydrogen, and optionally, two R* groups from Z (when R* is not hydrogen), or an R* group from Z and an R* group from Y form a ring system; where p is 0, q is 1, M is in the +2 formal oxidation state, and X' is 1,4-diphenyl-1,3-butadiene, 1,3-pentadiene or 2,4-hexadiene.

4. The metal complex of claim 3 wherein Z* is $SiR^*_2$ and Y is NR* and M is titanium or zirconium.

5. The metal complex of claim 4 corresponding to the formula:

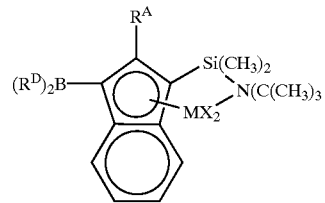

wherein $R^D$ is N,N-dimethylamino or N,N-diisopropylamino, $R^A$ is methyl or hydrogen, M is titanium, and X is cloride or methyl.

* * * * *

UNITED STATES PATENT AND TRADEMARK OFFICE
CERTIFICATE OF CORRECTION

PATENT NO.     : 6,420,299 B1                                           Page 1 of 1
DATED          : July 16, 2002
INVENTOR(S)    : D. Patrick Green, Francis J. Timmers and William J. Kruper Jr.

It is certified that error appears in the above-identified patent and that said Letters Patent is hereby corrected as shown below:

Column 19,
Line 8, "Z," should read -- 2, --.

Signed and Sealed this

Twenty-second Day of July, 2003

JAMES E. ROGAN
*Director of the United States Patent and Trademark Office*